United States Patent [19]

Bonnet

[11] 4,137,920

[45] Feb. 6, 1979

[54] ENDOSCOPES

[75] Inventor: Ludwig Bonnet, Knittlingen, Fed. Rep. of Germany

[73] Assignee: Richarg Wolf GmbH, Knittlingen, Fed. Rep. of Germany

[21] Appl. No.: 759,718

[22] Filed: Jan. 17, 1977

[30] Foreign Application Priority Data

Jan. 20, 1976 [DE] Fed. Rep. of Germany ....... 2601802

[51] Int. Cl.[2] .............................................. A61B 17/32

[52] U.S. Cl. ........................................ 128/311; 128/7; 128/305

[58] Field of Search ................... 128/4, 6, 7, 8, 303 R, 128/305, 303.14, 311, 328, 2 B, 214.4, 7 R, 4 R, 303.15

[56] References Cited

U.S. PATENT DOCUMENTS

| | | | |
|---|---|---|---|
| 2,031,020 | 2/1936 | Wappler | 128/7 |
| 2,708,437 | 5/1955 | Hutchins | 128/7 |
| 2,888,017 | 5/1959 | Wallace | 128/7 |
| 2,990,830 | 7/1961 | Hett | 128/4 |
| 3,606,878 | 9/1971 | Kellogg, Jr. | 128/305 |
| 3,835,854 | 9/1974 | Jewett | 128/214.4 |
| 3,850,175 | 11/1974 | Iglesias | 128/7 R X |
| 4,011,869 | 3/1977 | Seiler, Jr. | 128/305 |

FOREIGN PATENT DOCUMENTS

| | | | |
|---|---|---|---|
| 7336834 | 1/1974 | Fed. Rep. of Germany. | |
| 2249641 | 5/1974 | France | 128/7 |

*Primary Examiner*—Henry J. Recla

*Attorney, Agent, or Firm*—Kinzer, Plyer, Dorn & McEachran

[57] ABSTRACT

Endoscope instrument assembly in which a dual channel guide member, containing a telescope in one channel and a support for a slitting blade in the other channel, is displaceable from an inner barrel and replaceable by a separate elongated tube which is sized to receive the same telescope and which has at its distal end an annular cutting edge.

5 Claims, 5 Drawing Figures

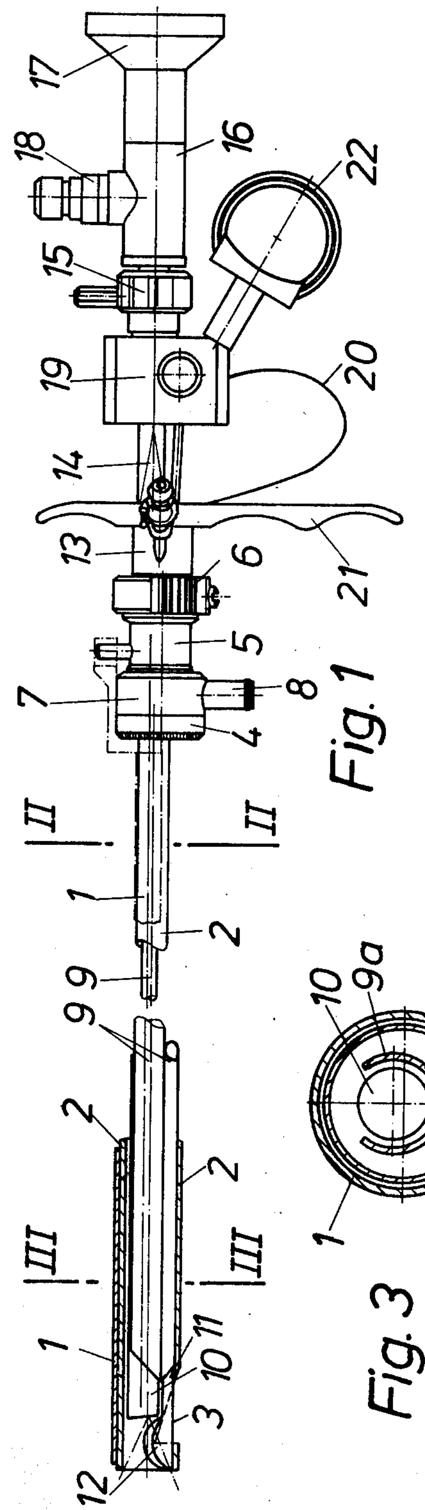
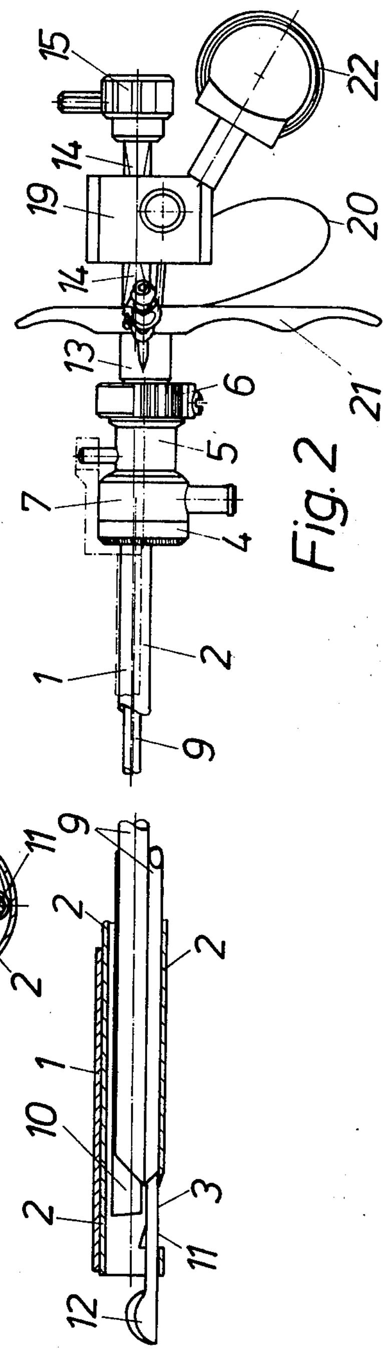

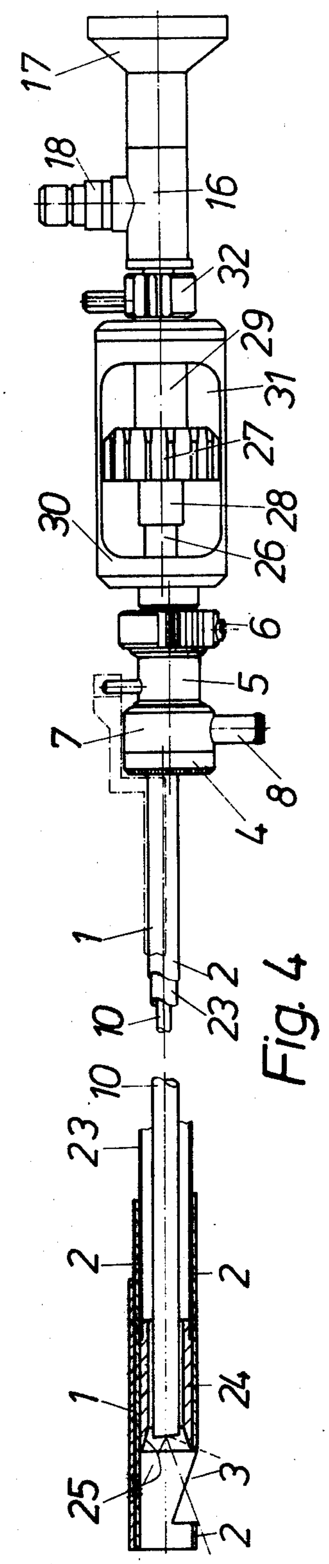
Fig. 4
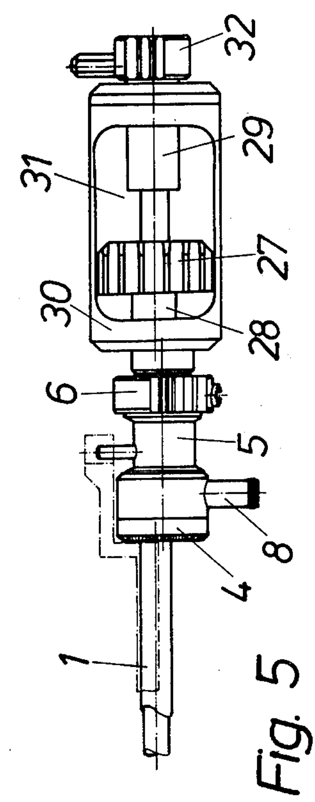
Fig. 5
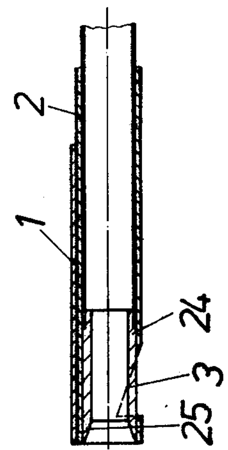

ENDOSCOPES

BACKGROUND OF THE INVENTION

The present invention relates to endoscopes for treating strictures in the urinary passage, of the kind comprising an outer barrel which is open at the bottom for its entire length, with the width of the opening at least corresponding to the diameter of an implant catheter to be inserted in the bladder, a telescope which can be inserted in the outer barrel, and a blade movable in the distal direction for slitting the stricture. Hereinafter such endoscopes will be referred to as "of the kind described".

Strictures in the urinary passage are slit open by an endoscopic operation, while under observation, by means of an endoscope comprising an outer barrel, an examination barrel and an operating barrel, and to prevent a fresh constriction from developing during healing, an implant catheter of a known kind is inserted through the urinary passage and into the bladder. To allow this pliable implant or balloon catheter to be inserted without difficulty, use is made of an endoscope having an outer barrel, as described for example in German Gebrauchsmuster No. 7,339,606, which is open on the underside for its entire length across a width corresponding to the diameter of the catheter. In this way the outer barrel can be used to insert the catheter an can then be withdrawn again while leaving the catheter in place in the urinary passage. The catheter, which remains in place until the stricture has healed, provides an avenue for urine to flow through but in the region concerned there is heavy scarring in the urinary passage and the opening in it is not round. The danger therefore exists that because of the scarring the passage will become smaller again in the course of time and the operation will have to be repeated.

It is therefore an object of the invention to create an opening of circular cross-section in the urinary passage after a stricture in the passage has been slit open and thus to avoid repeated operations as far as possible.

SUMMARY OF THE INVENTION

This object is achieved by providing, in an endoscope of the kind described, an inner guide barrel capable of insertion in said outer barrel, said guide barrel being open at its distal end, and provided on its underside with a window cut-out at a point rearwardly of said distal end, said guide barrel being provided with coupling means at its proximal end and arranged to receive an inner tube in turn being arranged to receive said telescope, and having an annular blade at its distal end and an operating knob at its proximal end for turning and displacing said inner tube to enable said annular blade to move within limits across the region occupied by said window cut-out.

This manner of achieving the object makes it possible for all the fragments which project from the passage wall, after the prior slitting of the stricture, to be cut or bored away (reamed) by rotation and forward movement of the annular blade at the distal end of the inner tube, until a virtually circular opening is created corresponding in diameter to the inner tube. After this the inner guide barrel and the inner tube are withdrawn from the outer barrel and an implant catheter is introduced into the bladder through the outer barrel and finally the outer barrel is withdrawn, the catheter then remaining in place in the bladder and urinary passage until the stricture which has been operated on is fully healed.

So that the fewest possible interchangeable barrels need be used and an examination barrel can be dispensed with, it is further proposed in accordance with the invention that there be insertable in the guide barrel, a guide for the examination telescope and for a support wire with a distal slitting blade, which wire can be shifted axially by means of a proximal handle, and that the guide be interchangeable with the tube.

It is however also possible to use an endoscope as disclosed in German Gebrauchsmuster No. 7,339,606, with which the stricture is first examined using an examination barrel and the examination barrel is then exchanged for an operating barrel with a slitting blade. After the stricture has been slit, the operating barrel is exchanged for the guide barrel and the inner barrel, and annular blade according to the invention to allow an opening of circular cross-section to be produced at the site of the operation.

BRIEF DESCRIPTION OF THE DRAWINGS

In order that the invention may be more clearly understood, reference will now be made to the accompanying drawings which show one embodiment thereof by way of example and in which:-

FIG. 1 is a side-view of the endoscope, with the distal end shown enlarged in longitudinal section, and it shows inserted in the outer barrel, the guide for the telescope and the wire carrying the distal slitting blade in the rest position,

FIG. 2 is a similar side-view, with the distal end shown in longitudinal section but with the slitting blade advanced,

FIG. 3 is an enlarged cross-section on line III—III of FIG. 1,

FIG. 4 is a side-view, with the distal end shown enlarged in longitudinal section, and it shows inserted in the guide barrel and in the rest position, the tube with its annular blade, and

FIG. 5 is a side-view corresponding to FIG. 4 showing the distal end in longitudinal section with the annular blade advanced.

DETAILED DESCRIPTION OF A PREFERRED EMBODIMENT

The embodiment of the endoscope shown in the drawings consists of an outer barrel 1 which may be of any known kind, open at the bottom for its entire length, with the width of the opening at least corresponding to the diameter of an implant or balloon catheter to be inserted in the bladder.

Into the outer barrel is inserted an inner guide barrel 2 which is open at the distal end and which is provided with an open cut-out (window) at the bottom at a point rearwardly of the distal end. The guide barrel 2 is coupled to the outer barrel proximally by an eccentric ring 4. Proximally the guide barrel 2 is provided with a machine-turned portion 5 and a bayonet connector 6. Mounted on portion 5 is a ring 7 which is provided with a flushing connection 8, via which flushing water can be fed through the guide barrel 2 to its open distal end.

A guide 9 for an examination telescope characterized by the usual sight tube 10, and for a pressure and traction resistant wire 11, can be inserted in the guide barrel 2. The guide 9 consists for example of a guide tube 9*a* (FIG. 3) which has a channel open at the top and to which a tube having a lower channel of smaller diameter to guide the wire 11 is connected in dependent relation therebeneath. The gap between the guide 9 and the guide barrel 2 acts as a flushing passage. At the distal end the wire 11 is provided with a longitudinally orientated slitting blade 12.

Proximally, the guide 9 is provided with a connector 13 having a wall coupling for connection to connector 6. Its upper part 9*a* extends into a square guide 14 and at the proximal end is provided with a bayonet connector 15 to allow a tubular member 16 at the proximal end of the telescope sight tube 10 and the eye-piece 17 to be coupled on. The member 16 is also used to connect on a light conductor which leads through a connection 18 to the distal end of the telescope.

Displaceably mounted on the guide 14 is a slider 19 which is connected to the proximal end of the bladed wire 11 and which, in the rest position, is held against a part 15, which acts as a stop, by a leaf spring 20. The tapered connector 13 is provided with a grip 21 and the slider 19 with a finger or thumbs grip 22. By holding the grip 21 and using the grip 22 the slider 19 can be moved in the distal direction. The wire 11 is thus moved in the longitudinal direction and the stricture can thus be slit open by means of the slitting blade 12 while under observation. The position involved is shown in FIG. 2.

After the stricture has been slit open, the bayonet connector 6 is released and the guide 9, together with the telescope sight tube 10, the wire 11 and its blade 12, and the associated proximal parts 13 to 22, is withdrawn from the guide barrel 2 and the telescope is withdrawn from the guide 9 by releasing the bayonet connector 15.

As inner replacement guide tube 23 (FIGS. 4 and 5) which has an annular blade 24 provided at its distal end is then inserted in the guide barrel 2, which has remained in place in the outer barrel 1. At its distal end the annular blade has an outwardly tapering cutting edge 25 which, in the rest position, is situated just to the rear of the window cut-out 3. Proximally the inner guide tube 23 is provided with a strengthening guide-sleeve 26, on which is fixed an easily gripped cylindrical knob 27 having a collar 28, and it is displaceably mounted in a guide bushing 29. A cylindrical housing 30 containing two large opposing open cut-outs 31 fits round the knob 27 and part of the guide sleeve 26 and at the distal end it is detachably connected to the bayonet connector 6 on the guide barrel 2.

The telescope sight tube 10 mentioned in connection with FIGS. 1 to 3, which has proximal connecting parts 16 to 18, is passed through the inner guide tube 23 and is locked in place by means of a connector 32. When the site of the operation where the slit has been cut is being made round, the cut-out 3 in the guide barrel 2 lies in the area of the site of operation; and the inner guide tube 23 is then moved in the distal direction by means of the knob 27 along the length of the cut-out 3 while being turned, when whereby the projecting fragments of the slit stricture are cut away by the cutting edge 25 of the annular blade 24.

By successively turning the whole endoscope, and thus the cut-out or window 3, and moving the annular blade alternately backwards and forwards, a round opening is cut in the urinary tube for the length of travel of the blade. Then, as dictated by the length of the stricture, the entire endoscope is moved forwards in steps corresponding to the length of travel of the annular blade, with the rotary and reciprocating movements of the annular blade referred to above being repeated, until a virtually circular opening has been shaved out or reamed along the length of the slit stricture, flushing naturally being maintained for the whole time.

What I claim is:

1. In an endoscope instrument assembly for treating strictures in the urinary passage, including an outer barrel with a slot along the length having a width at least equal to the diameter of an implant catheter to be introduced through the outer barrel slot for insertion into the bladder, and having a slitting blade attached to an elongated support to be movable axially in the distal direction relative to the outer barrel for slitting the stricture while under observation with the aid of a telescope having an elongated sighting tube, an inner barrel removably supported within said outer barrel and provided at its distal end with an aperture facing the slot of the outer barrel, a one-piece dual channel guide member removably supported within the inner barrel and having dual channels respectively presented by elongated tubular elements in which are positioned, in radial spaced relation, both the telescope and the support for the slitting blade and wherein the length of the elongated sight tube is approximately equal to the length of said dual channel guide member tubular elements, the improvement comprising: a separate elongated tube insertable in said inner barrel upon removal of said guide member together with said telescope sight tube and the support for the slitting blade, means enabling said separate elongated tube to be rotatable and axially movable within said inner barrel and said separate elongated tube being provided with an annular blade at its distal end, said separated elongated tube being of such length that when inserted within the inner barrel the annular blade thereon may be positioned within said aperture to work axially and rotatably on the portion of the urinary passage exposed by said aperture of the inner barrel, said telescope sight tube being removable from said guide member and insertable into said separate elongated tube, the inner diameter of said separate elongated tube being approximately equal the outer diameter of said telescope sight tube so the latter may fit within the inner diameter of said separate elongated tube, whereby the guide member together with the telescope sight tube and the support for said slitting blade may be removed from the inner barrel, after slitting the stricture, and replaced by said separate elongated tube, having the annular blade and having the telescope sight tube fitted therein, to enable the urinary passage area around the slit structure to be reamed by the annular blade with the aid of the telescope.

2. The instrument assembly as defined in claim 1 in which said separate elongated tube bearing the annular knife is provided with a knob which enables said separate elongated tube and its annular knife to be displaced during an operation.

3. The instrument assembly as defined in claim 2 in which the support for the slitting knife is connected proximally to a manually operable slide slidably mounted on a flat sided guide supported by said dual channel guide member, said slide being biased into a proximal terminal position by a spring attached thereto at one end and attached at the opposite end to a fixed other part of the instrument assembly.

4. The instrument assembly as defined in claim 2 in which the knob is surrounded by a cylindrical housing having opposed openings through which the knob may be grasped.

5. The instrument assembly as defined in claim 1 in which there is an open area between the inner barrel and the dual guide, which area is connected proximally to a flushing stud on the instrument assembly enabling flushing liquid to be introduced into said open area.

* * * * *